United States Patent
Norris

(10) Patent No.: US 9,830,429 B2
(45) Date of Patent: Nov. 28, 2017

(54) SYSTEMS AND METHODS FOR MULTI-FLUX COLOR MATCHING

(71) Applicant: PPG Industries Ohio, Inc., Cleveland, OH (US)

(72) Inventor: Alison M. Norris, Avon, OH (US)

(73) Assignee: PPG Industries Ohio, Inc., Cleveland, OH (US)

(*) Notice: Subject to any disclaimer, the term of this patent is extended or adjusted under 35 U.S.C. 154(b) by 958 days.

(21) Appl. No.: 13/802,939

(22) Filed: Mar. 14, 2013

(65) Prior Publication Data

US 2014/0278251 A1    Sep. 18, 2014

(51) Int. Cl.
| | | |
|---|---|---|
| *G06F 19/00* | (2011.01) | |
| *G01J 3/46* | (2006.01) | |
| *G01J 3/50* | (2006.01) | |
| *G01J 5/52* | (2006.01) | |
| *B01F 15/00* | (2006.01) | |
| *G01J 3/52* | (2006.01) | |

(52) U.S. Cl.
CPC ............ *G06F 19/703* (2013.01); *G01J 3/463* (2013.01); *G01J 3/504* (2013.01); *B01F 15/00214* (2013.01); *G01J 3/524* (2013.01)

(58) Field of Classification Search
CPC .................................................... G06F 19/703
USPC ......................................................... 702/189
See application file for complete search history.

(56) References Cited

U.S. PATENT DOCUMENTS

| | | | |
|---|---|---|---|
| 3,690,771 A | | 9/1972 | Armstrong, Jr. et al. |
| 4,635,213 A | * | 1/1987 | Murata et al. ................. 382/111 |
| 6,362,885 B1 | * | 3/2002 | Osumi ....................... G01J 3/46 |
| | | | 356/402 |
| 6,539,325 B1 | * | 3/2003 | Numata et al. ............... 702/127 |

(Continued)

FOREIGN PATENT DOCUMENTS

| | | | |
|---|---|---|---|
| GB | | 1103950 | 2/1968 |
| GB | | 1103950 A * | 2/1968 |
| WO | WO 2010/036874 A1 | | 4/2010 |

OTHER PUBLICATIONS

Aspland et al., "Color Technology in the textile industry", 1997, American Association of Textile Chemists and Colorists, Second Edition.*

(Continued)

*Primary Examiner* — Janet Suglo
*Assistant Examiner* — Michael Dalbo
(74) *Attorney, Agent, or Firm* — Michael D. Lazzara

(57) ABSTRACT

A computer implemented method. The method includes generating, using a processor, a set of calibration data relating to a plurality of pigments that are present in a collection of coatings. Generating includes calculating an absorption/reflectance relationship of a plurality of samples coated with a plurality of the pigments, wherein calculating includes using a color matching calculation, and calculating a plurality of concentrations of a non-standard pigment. Generating also includes plotting a relationship between the concentrations and the absorption/reflectance relationships, and determining a correlation of the concentrations for a plurality of Fresnel coefficients relating to the samples. The method further includes determining, using the processor, a coating formulation of a target coating based on the correlation.

11 Claims, 7 Drawing Sheets

(56) References Cited

U.S. PATENT DOCUMENTS 7,167,246 B1 1/2007 Skierski
2011/0160892 A1 6/2011 Kettler

OTHER PUBLICATIONS

Kenyon, "The Light Fantastic: A Modern Introduction to Classical and Quantum Optics", 2008, Oxford University Press.*
Berssenbrügge et al., P., "Color recipe prediction for facial episthesis materials", 2012, XP007922773, DGaO Proceedings.
X-Rite, Inc., "Color iQC and Color iMatch Multi Flux Matching Guide", Jul. 30, 2012, Version 8.0, 19 pages.
Billmeyer, Jr., Fred W. and Saltzman, Max, "Principles of Color Technology", Second Edition, 1981, pp. 133-192.

* cited by examiner

EXAMPLE GRADATION OF COLOR ACROSS CALIBRATION SERIES

SYSTEMS AND METHODS FOR MULTI-FLUX COLOR MATCHING

FIELD OF THE INVENTION

In various embodiments, the present invention generally relates to the inclusion of many fluxes, (i.e., a multi-flux), of optical reflections from a target coating to correct and enhance the spectrophotometrically measured reflectance curve for color matching purposes.

BACKGROUND OF THE INVENTION

Kubelka-Munk theory is oftentimes used to analyze the diffuse reflective spectra from a coating on a target surface. The use of the two-flux approximation Kubelka Munk equations for color-matching a coating on the target surface generally requires two primary assumptions. First, the refractive index of the sample being measured is the same as the refractive index of air. To correct the refractive index assumption, the Saunderson correction equation is employed. The Saunderson correction equation employs the use of two Fresnel coefficients, K1 and K2, which take into account the refractive index of the coated surface in question. As used herein, the K1 coefficient represents the fractional reflectance when light entering the target sample is partially reflected at the sample surface and the K2 coefficient represents the fractional reflectance when light exiting the sample is partially reflected back into the sample at the sample surface. The second assumption is that 100% of the incident light on the coated surface is either absorbed or scattered by the coating in a uniform manner, leaving no edge effects. This assumption further results in the expectation of a linear relationship between K (absorption) and S (scattering), "K/S", of the pigment over the concentration range of that pigment's usage and that the relationship will be the same across all viewing angles.

The two-flux approximation Kubelka-Munk equations are sufficient for characterization of solid, opaque dispersed pigmentations coated to opacity. However, with the introduction and subsequent rise in desirability and popularity of gonioapparent special effect pigments and highly transparent dispersed pigments and dyes, the two-flux approximation Kubelka-Munk theory breaks down.

In order to account for the aforementioned new pigment types and technologies, a pseudo-multiflux approach can be employed. Historically and in theory, the multiflux approach has been to allow the K2 Fresnel coefficient in the Saunderson equation, which converts measured reflectance to internal reflectance, to vary dependent on wavelength. Also, the variation of the K1 Fresnel coefficient by wavelength has been employed as well.

Thus, there is a need for a system and process that varies the K1 and K2 Fresnel coefficients by wavelength, angle and concentration such that the K1 and K2 values become functions of concentration, given a particular angle and wavelength combination.

SUMMARY OF THE INVENTION

In a first aspect, embodiments of the invention provide a computer implemented method. The method includes generating, using a processor, a set of calibration data relating to a plurality of pigments that are present in a collection of coatings. Generating includes calculating an absorption/reflectance relationship of a plurality of samples coated with a plurality of the pigments, wherein calculating includes using a color matching calculation, and calculating a plurality of concentrations of a non-standard pigment. Generating also includes plotting a relationship between the concentrations and the absorption/reflectance relationships, and determining a correlation of the concentrations for a plurality of Fresnel coefficients relating to the samples. The method further includes determining, using the processor, a coating formulation of a target coating based on the correlation.

In another aspect, embodiments of the invention are directed to a system. The system includes a user interface and a processor in communication with the user interface. The processor is programmed to generate a set of calibration data relating to a plurality of pigments that are present in a collection of coatings, wherein generating includes calculating an absorption/reflectance relationship of a plurality of samples coated with a plurality of the pigments, wherein calculating includes using a color matching calculation, calculating a plurality of concentrations of a non-standard pigment, plotting a relationship between the concentrations and the absorption/reflectance relationships, and determining a correlation of the concentrations for a plurality of Fresnel coefficients relating to the samples. The processor is further programmed to determine a coating formulation of a target coating based on the correlation.

In another aspect, embodiments of the invention provide an apparatus. The apparatus includes means for generating a set of calibration data relating to a plurality of pigments that are present in a collection of coatings, wherein the means for generating includes means for calculating an absorption/reflectance relationship of a plurality of samples coated with a plurality of the pigments, wherein calculating includes using a color matching calculation, means for calculating a plurality of concentrations of a non-standard pigment, means for plotting a relationship between the concentrations and the absorption/reflectance relationships, and means for determining a correlation of the concentrations for a plurality of Fresnel coefficients relating to the samples. The apparatus also includes means for determining a coating formulation of a target coating based on the correlation.

In a further aspect, embodiments of the invention provide a non-transitory computer readable medium including software for causing a processor to:
  generate a set of calibration data relating to a plurality of pigments that are present in a collection of coatings, wherein generating includes:
    calculating an absorption/reflectance relationship of a plurality of samples coated with a plurality of the pigments, wherein calculating includes using a color matching calculation;
    calculating a plurality of concentrations of a non-standard pigment;
    plotting a relationship between the concentrations and the absorption/reflectance relationships;
    determining a correlation of the concentrations for a plurality of Fresnel coefficients relating to the samples; and
  determine a coating formulation of a target coating based on the correlation.

DETAILED DESCRIPTION OF THE INVENTION

In various aspects, embodiments of the present invention are directed to systems and methods that improve and correct the Saunderson conversion of measured spectral reflectance into internal reflectance for use with a color matching methodology, for example the Kubelka-Munk methodology, in order to formulate and adjust pigmentations to match a target coating. Embodiments of the invention include an apparatus that has a device for capturing information for the target sample and a database of K1 and K2 Fresnel coefficients that are used to create improved formulations and formula adjustments. As used herein, the K1 coefficient represents the fractional reflectance when light entering the target sample is partially reflected at the sample surface and the K2 coefficient represents the fractional reflectance when light exiting the sample is partially reflected back into the sample at the sample surface.

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Figure 1:
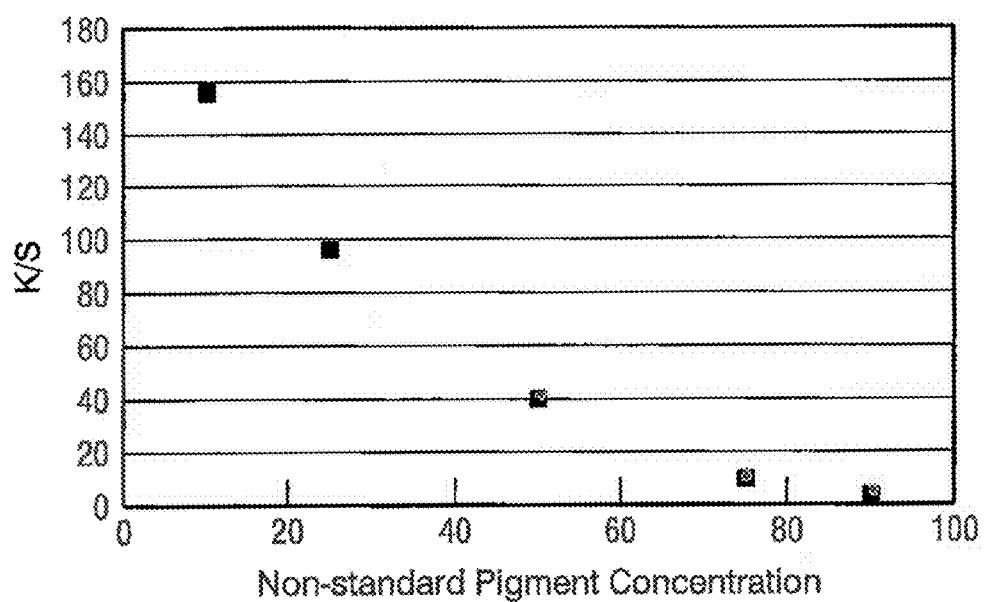
FIG. 1 is a graph illustrating a concentration vs. K/S relationship using fixed K1 and K2 values for the 45 degree angle at 500 nm of a white mica.

Current methodologies that use, for example, the Kubelka-Munk or other approximation algorithm do not work for gonioapparent pigments and highly transparent dispersed pigments and dyes. FIG. 1 is a graph illustrating a concentration vs. K/S relationship using fixed K1 and K2 values for the 45 degree angle at 500 nm of a white mica. As illustrated, the curvature of the relationship is a violation of the second primary assumption for use in a two-flux Kubelka-Munk or other process. In order to correct the relationship in the second primary assumption, the first primary assumption using the Fresnel coefficients in the Saunderson equation is employed as discussed in subsequent paragraphs.

Figure 2:
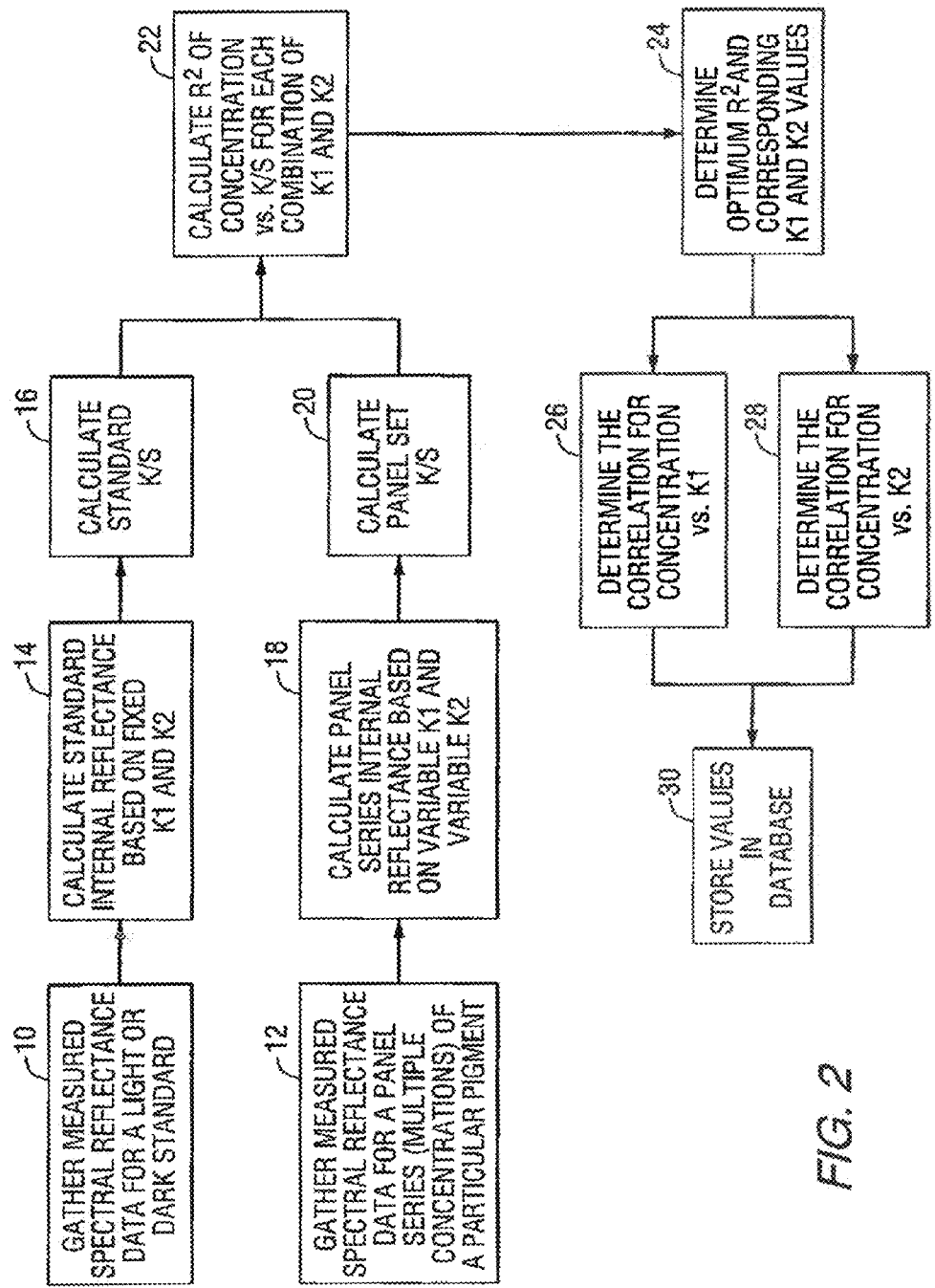
FIG. 2 illustrates an embodiment of a process for building a set of calibration data for a full paint system.

FIG. 2 illustrates an embodiment of a process for building a set of calibration data for a full paint system. The calibrations can be thought of as "fingerprints" of the individual pigments within a paint system. In various embodiments, it is expected that there will be standard solid, dispersed pigmentations as well as gonioapparent special effect pigments and highly transparent dispersed pigments or dyes.

In order to start the calibration process, at step 10 a light standard and a dark standard are chosen. Examples of a light standard may include, but are not limited to, an opaque dispersed white, an aluminum, or a white pearl. Examples of a dark standard may include, but are not limited to, an opaque dispersed black pigment or polished black glass. In various embodiments, an assumption is employed for the light standard across all angles of analysis: The light standard will scatter 100% of light and absorb 0% of light for all angles of inspection. Similarly, in various embodiments a dark standard has the assumption that it scatters 0% of light and absorbs 100% of light. Each of the two standards may be individually coated to opacity and measured with a spectrophotometer. The light standard maintains a scattering, S, value of 1 and an absorbing, K, value of 0. The light standard also has a fixed K1 and K2 value. Similarly, the dark standard maintains a scattering, S, value of 0 and an absorbing, K, value of 1. The dark standard has fixed K1 and K2 values. By way of example, the fixed K1 and K2 values for the standards may be set: (i) based on the refractive indices of the light or dark standard formulations, (ii) based on historical usages or textbook suggestions; or (iii) set simply as 0 and 0.

Figure 4:
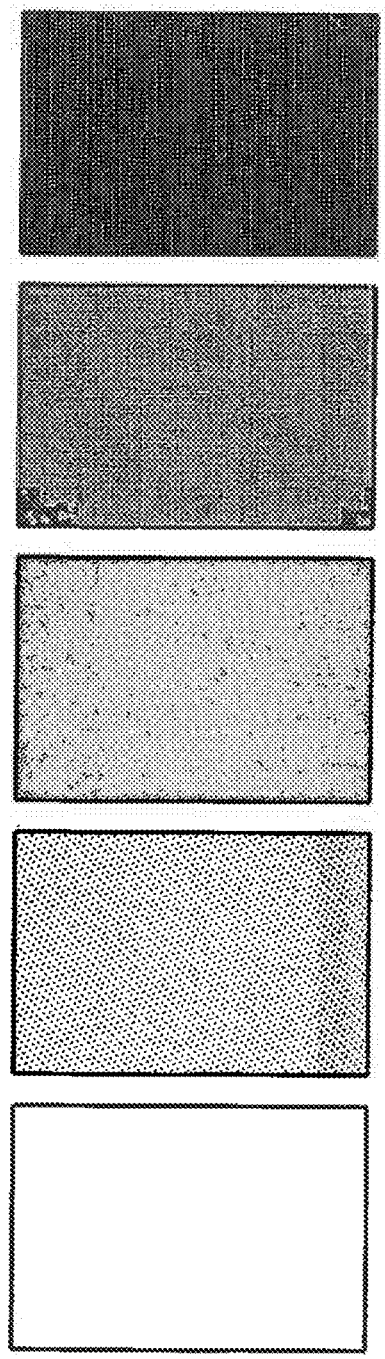
FIG. 4 illustrates a gradation of color across multiple panels.

At step 12 a series of panels for each individual pigmentation within the system are created by creating at least binary or tertiary mixtures. For normal, solid, dispersed pigments, the binary or tertiary mixtures are multiple levels of the individual pigment mixed with the light standard. Mixtures can be made by volume additions, weight additions, or pigment weight percent, as long as the desired outcome of a gradation of color across multiple panels is achieved, as the example in FIG. 4 shows. For example, a binary mixture of a red shade phthalocyanine blue with a light standard may take the form of the following weight percentages: 95% light standard with 5% blue, 75% light standard with 25% blue, 50% light standard with 50% blue, 25% light standard with 75% blue, and 5% light standard with 95% blue. In various embodiments, it may be desirable to have multiple mixtures nearer the 100%/0% and 0%/100% thresholds, or other points of color saturation. The dark standard may have a panel series created using the light standard. The mixtures are then individually coated to opacity and measured with a spectrophotometer. For gonioapparent pigmentations and highly transparent dispersions or dyes, the individual pigment may be mixed in the same binary or tertiary fashion as described hereinabove, but using the dark standard instead of the light standard. These mixtures are again coated to opacity and measured with a spectrophotometer. Additionally, due to the nature of high hue angle color travel of some gonioapparent pigments, it may be desired in various embodiments to have a masstone, or single pigment coating, not necessarily to opacity over a light standard (coated to opacity) base to further characterize the individual pigment.

Once the series of panels have been created for every desired pigment within the paint system, at step 14 the internal reflectance of the light or dark standard is calculated using the Saunderson equation, fixed K1 and K2 values, and the measured spectral reflectance data from the masstone only (100%) light or dark standard.

Using the calculated internal reflectance values, a color matching theory such as, for example, the Kubelka-Munk theory or other theory, is used to calculate the K/S values of the light or dark standard at step 16.

The internal reflectance of the non-standard pigment series is calculated at step 18. There are three methods that may be used for the calculation: (1) allow K1 to vary by angle, wavelength, and concentration while K2 remains fixed; (2) allow K1 to remain fixed while K2 varies by angle, wavelength, and concentration; and (3) allow both K1 and K2 to vary by angle, wavelength, and concentration. In various embodiments, in order to find the optimal solution, all three methods are used and the best result of the three is chosen. The variation of K1 and K2 is the correction to the first primary assumption of the two-flux Kubelka-Munk, or other, approximation. Additionally, in various embodiments the range within which the K1 and K2 values is allowed to vary may be manipulated based on prior knowledge, such as by using refractive indices of the formula in question, or knowledge gained within the optimization process. In various embodiments a large range of K1 and K2 variation values and a small increment between the variations is allowed so that the global optimum is found, rather than a local optimum. The global optimum may or may not be similar to the calculated K1 and K2 value based on the refractive index.

Figure 5:
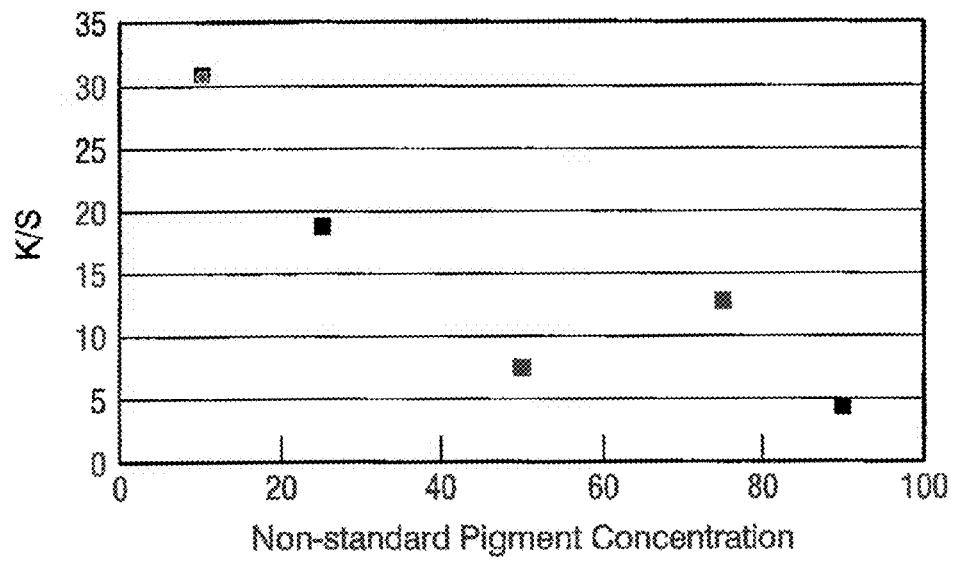
FIG. 5 illustrates and example of a graph of concentration versus K/S for the 500 nm wavelength of a white mica at a 45 degree angle using a specific set of K1 and K2 from within the variable set of data.

In various embodiments, by allowing K1 and K2 to vary, multiple sets of internal reflectance curves are created. In various embodiments, all scenarios may be examined by using all concentrations. In various embodiments, if accuracy can be improved by not using one or more concentrations, then such a course of action may be taken at a cost to the final functionality color matching algorithm. At step 20 multiple sets of color matching K/S data are calculated based on the multiple corresponding sets of internal reflectance curves that have been calculated. At step 22 the concentration of the non-standard pigment is plotted against the K/S value for each particular combination of K1 and K2 at a given angle and wavelength. In various embodiments linearization is sought to create improved performance within color matching equations at step 24, the linear optimum $R^2$ value, closest to 1 or −1, is chosen. The choice of an optimum $R^2$ value subsequently chooses the corresponding set of K/S data and internal reflectance values, which correspond to a particular set of K1 and K2 values. FIG. 5 illustrates and example of a graph of concentration versus K/S for the 500 nm wavelength of a white mica at a 45 degree angle using a specific set of K1 and K2 from within the variable set of data. The $R^2$ illustrated is roughly 0.75 and the relationship between concentration and K/S is linear, which conforms to the second primary assumption of the two-flux Kubelka-Munk, or other, approximation.

Figure 6:
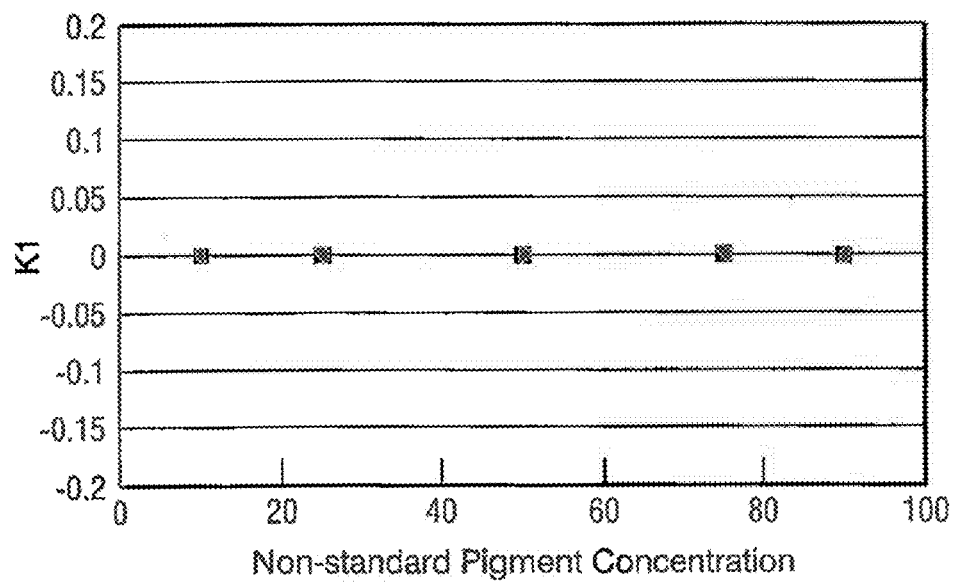
FIGS. 6 and 7 illustrate examples of two types of graphs for the same 500 nm wavelength of the 45 degree angle of a white mica.
Figure 7:
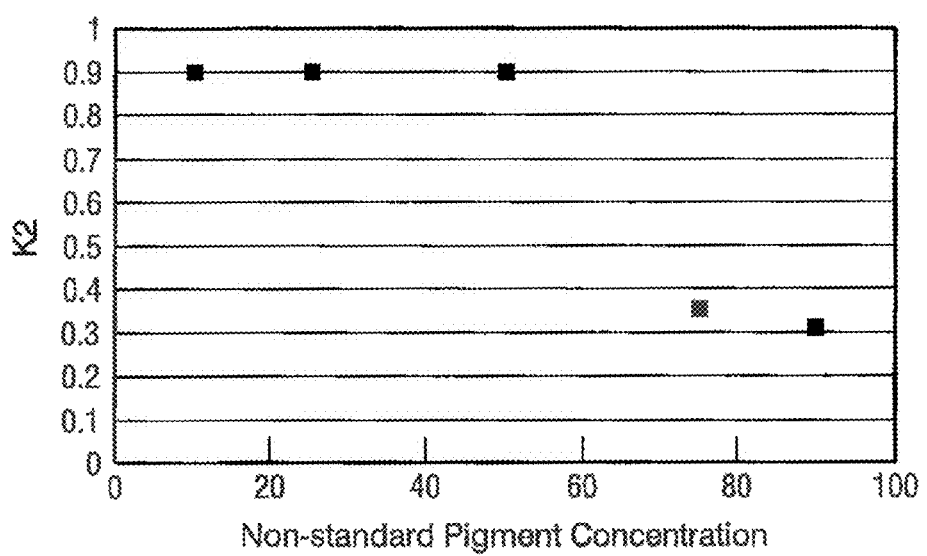

Because the K1 and K2 values are allowed to vary by concentration as well as angle and wavelength in various embodiments, there may be multiple values for K1 and K2 for a single pigmentation. The K1 and K2 values for each concentration of the non-standard pigment that have been chosen based on the optimal concentration vs. K/S graph are taken into consideration. At steps 26 and 28 the concentration of the non-standard pigment individually against the K1 and K2 values chosen from the original K/S optimization is plotted, resulting in two graphs/curves. In various embodiments the K1 and K2 values may be individually defined by the concentration using a linear correlation, a non-linear correlation, or a stepwise linear or non-linear correlation. Examples of these two types of graphs for the same 500 nm wavelength of the 45 degree angle of a white mica are shown in FIGS. 6 and 7.

In various embodiments the process of calculating global optimal K1 and K2 values by concentration and wavelength is iterated over every available angle. Significant differences may be seen between angular data, especially when dealing with gonioapparent pigments, due to their nature of high color travel.

At step 30 all correlations for calculating K1 and K2 as a function of concentration for each specific angle and wavelength combination are stored in a database.

Figure 3:
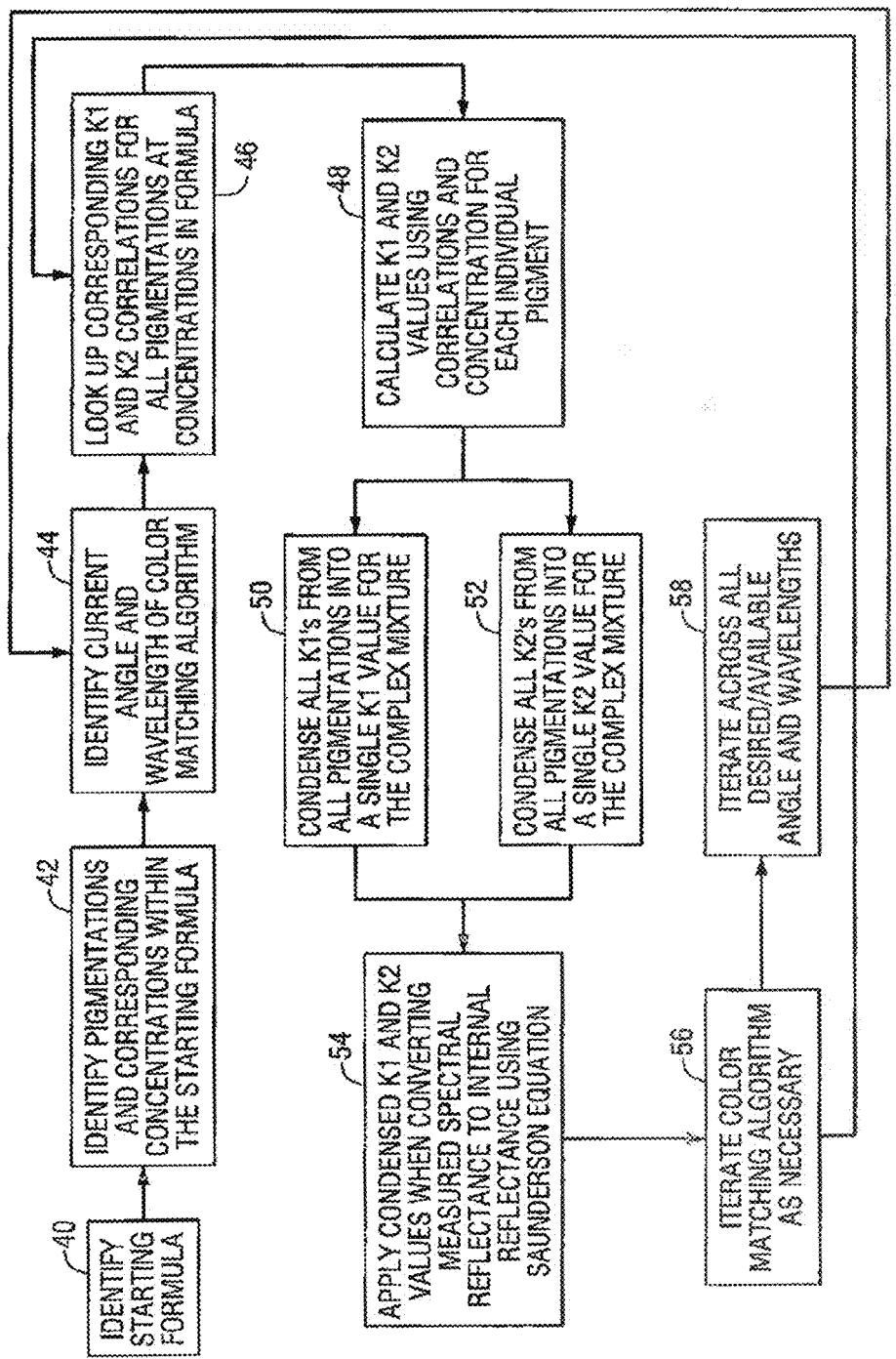
FIG. 3 illustrates a color matching process according to various embodiments.

Now that the optimized K1 and K2 values for each pigment within the paint system have been identified and stored in a database, standard color matching, such as Kubelka-Munk or other algorithms, may take place as illustrated in FIG. 3. As illustrated in FIG. 3, the multi-flux approach described herein using variable K1 and K2 Fresnel coefficients results in a slightly modified color matching methodology. Specifically, at steps 46, 48, 50 and 52 the proper K1 and K2 values for the particular angle, wavelength, and concentration are retrieved from a database, calculated, and condensed for use. When a conversion from measured spectral reflectance data is converted to internal reflectance, new K1 and K2 correlations are invoked. Thus, the K1 and K2 values are calculated dynamically during iteration of the process. In the case of unknown pigments in a starting formula, a close estimate of a similar formula is identified at step 40. The pigmentations within the similar formula are identified at step 42, and are used to define a starting set of K1 and K2 correlations and values at steps 44, 46 and 48.

For use in a complex mixture of multiple pigmentations, the multiple sets of K1 and K2 are combined into a singular set for the Saunderson calculation. In various embodiments, at steps 50 and 52 the condensation of the individual K1 and K2's by pigment may be achieved in various manners, and it can be determined which method is optimal. By way of example, methods of condensing multiple K1 and K2 values for multiple pigmentations in a complex mixture include: (i) simple average of all K1 values for the given iteration and simple average of all K2 values for the given iteration, (ii) weighted average of all the K1 values for the given iteration and weighted average of all K2 values for the given iteration; and (iii) statistical Pareto analysis to determine the most necessary K1 and K2 values and average. The Saunderson calculation is performed at step 54 and the process iterates as necessary at steps 56 and 58.

With the condensed K1 and condensed K2 values calculated, the standard equations of the two-flux Kubelka-Munk, or other, approximation may be employed with higher precision and accuracy when used with gonioapparent and highly transparent dispersed pigments and dyes.

Figure 8:
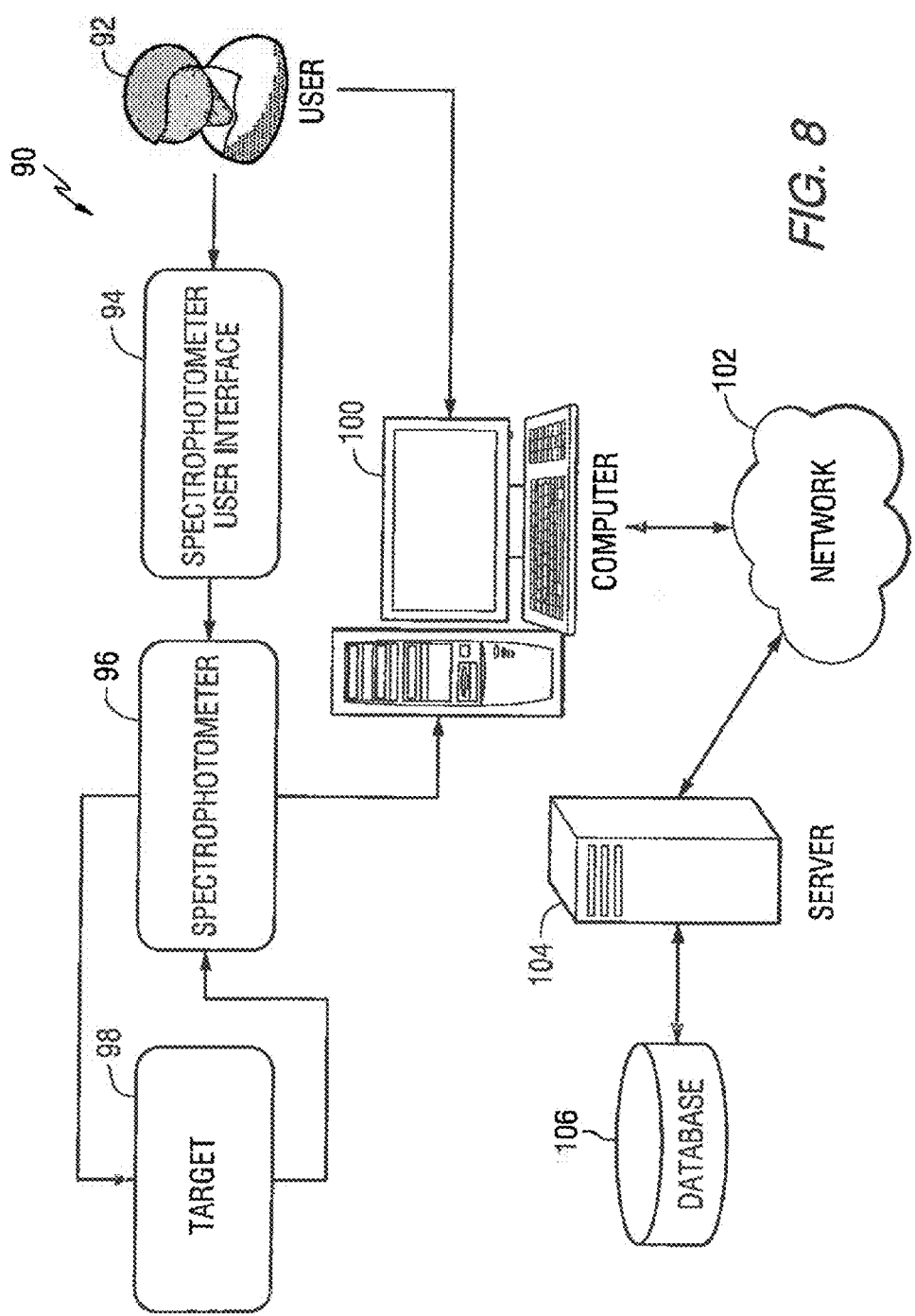
FIG. 8 illustrates an embodiment of a system which may be used to identify physical property attributes of a coating mixture of a target sample.

FIG. 8 illustrates an embodiment of a system 90 which may be used to identify physical property attributes of a coating mixture of a target sample. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may be in communication, via a network 102, with a server 104. The network 102 may be any type of network, such as the Internet, a local area network, an intranet, or a wireless network. The server 104 is in communication with a database 106 that may store the data and information that is used and generated by the methods of embodiments of the present invention. Various steps of the methods of embodiments of the present invention may be performed by the computer 100 and/or the server 106.

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

What is claimed is:

1. A computer implemented method, comprising:
receiving, with a spectrophotometer, spectral reflectance light reflected from a plurality of pigments present in a collection of coatings;
generating, using a processor, a set of calibration data relating to the plurality of pigments that are present in the collection of coatings, wherein generating includes:
converting at least a portion of the spectral reflectance light received by the spectrophotometer into spectral reflectance data;
converting the measured spectral reflectance data to internal reflectance data for use with a color matching calculation by using Saunderson conversion, wherein at least one of Fresnel coefficients K1, K2, or a combination thereof is varied by angle, wavelength, and concentration to yield multiple sets of internal reflectance data;
calculating multiple sets of absorption/reflectance data from the corresponding calculated multiple sets of internal reflectance data using a color matching calculation;
calculating a plurality of concentrations of a non-standard pigment;
plotting a relationship between the concentrations and the calculated absorption/reflectance data for each combination of K1 and K2 at a given angle and wavelength;
fitting the plotted data to identify a set of absorption/reflectance data corresponding to a set of K1 and K2 values; and
determining a correlation of the concentrations and each of the K1 and K2 values determined by the fitting of the plotted data;
determining, using the processor, a coating formulation of a target coating based on the correlation; and
creating a mixture in response to the determined coating formulation of the target coating.

2. The method of claim 1, further comprising outputting the coating formulation.

3. The method of claim 1, wherein the correlation is a best fit correlation.

4. A system, comprising:
a spectrophotometer programmed to receive spectral reflectance light reflected from a plurality of pigments present in a collection of coatings;
a user interface; and
a processor in communication with the user interface and programmed to:
generate a set of calibration data relating to the plurality of pigments that are present in the collection of coatings, wherein generating includes:
converting at least a portion of the spectral reflectance light received by the spectrophotometer into spectral reflectance data;
converting the measured spectral reflectance data to internal reflectance data for use with a color matching calculation by using Saunderson conversion, wherein at least one of Fresnel coefficients K1, K2, or a combination thereof is varied by angle, wavelength, and concentration to yield multiple sets of internal reflectance data;
calculating multiple sets of absorption/reflectance data from the corresponding calculated multiple sets of internal reflectance data using a color matching calculation;
calculating a plurality of concentrations of a non-standard pigment;
plotting a relationship between the concentrations and the calculated absorption/reflectance data for each combination of K1 and K2 at a given angle and wavelength;
fitting the plotted data to identify a set of absorption/reflectance data corresponding to a set of K1 and K2 values; and
determining a correlation of the concentrations and each of the K1 and K2 values determined by the fitting the plotted data;
determine a coating formulation of a target coating based on the correlation; and
creating a mixture in response to the determined coating formulation of the target coating.

5. The system of claim 4, further comprising a spectrophotometer in communication with the processor.

6. The system of claim 4, further comprising a database in communication with the processor.

7. The system of claim 4, wherein the processor is further programmed to output the coating formulation.

8. An apparatus, comprising:
means for receiving spectral reflectance light reflected from a plurality of pigments present in a collection of coatings;
means for generating a set of calibration data relating to a plurality of pigments that are present in a collection of coatings, wherein the means for generating includes:
means for converting the received spectral reflectance light into spectral reflectance data;
means for converting the measured spectral reflectance data to internal reflectance data for use with a color matching calculation by using Saunderson conversion, wherein at least one of Fresnel coefficients K1, K2, or a combination thereof is varied by angle, wavelength, and concentration to yield multiple sets of internal reflectance data;
means for calculating multiple sets of absorption/reflectance data from the corresponding calculated multiple sets of internal reflectance data using a color matching calculation;
means for calculating a plurality of concentrations of a non-standard pigment;
means for plotting a relationship between the concentrations and the calculated absorption/reflectance data for each combination of K1 and K2 at a given angle and wavelength;

means for fitting the plotted data to identify a set of absorption/reflectance data corresponding to a set of K1 and K2 values;

means for determining a correlation of the concentrations and each of the K1 and K2 values determined by the fitting of the plotted data;

means for determining, using the processor, a coating formulation of a target coating based on the correlation; and creating a mixture in response to the determined coating formulation of the target coating.

9. The apparatus of claim 8, further comprising means for outputting the coating formulation.

10. The apparatus of claim 8, wherein the correlation is a best fit correlation.

11. A non-transitory computer readable medium including software for causing a processor to:

cause a spectrophotometer to receive spectral reflectance light reflected from a plurality of pigments present in a collection of coatings;

generate a set of calibration data relating to the plurality of pigments that are present in the collection of coatings, wherein generating includes:

converting at least a portion of the spectral reflectance light received by the spectrophotometer into spectral reflectance data;

converting the measured spectral reflectance data to internal reflectance data for use with a color matching calculation by using Saunderson conversion, wherein at least one of Fresnel coefficients K1, K2, or a combination thereof is varied by angle, wavelength, and concentration to yield multiple sets of internal reflectance data;

calculating multiple sets of absorption/reflectance data from the corresponding calculated multiple sets of internal reflectance data using a color matching calculation;

calculating a plurality of concentrations of a non-standard pigment;

plotting a relationship between the concentrations and the calculated absorption/reflectance data for each combination of K1 and K2 at a given angle and wavelength;

fitting the plotted data to identify a set of absorption/reflectance data corresponding to a set of K1 and K2 values; and determining a correlation of the concentrations and each of the K1 and K2 values determined by the fitting of the plotted data;

determine a coating formulation of a target coating based on the correlation; and create a mixture in response to the determined coating formulation of the target coating.

* * * * *